United States Patent

Chimenti et al.

[11] Patent Number: 5,708,270
[45] Date of Patent: Jan. 13, 1998

[54] OPTIMIZATION OF ACID STRENGTH AND TOTAL ORGANIC CARBON IN ACID PROCESSES

[75] Inventors: Robert John Louis Chimenti, Short Hills; Gerald Martin Halpern, Bridgewater, both of N.J.; Bernie John Pafford, Baton Rouge, La.

[73] Assignee: Exxon Research and Engineering Company, Florham Park, N.J.

[21] Appl. No.: 688,320

[22] Filed: Jul. 30, 1996

Related U.S. Application Data

[60] Continuation of Ser. No. 412,239, Mar. 28, 1995, abandoned, which is a division of Ser. No. 125,060, Sep. 21, 1993, Pat. No. 5,426,053.

[51] Int. Cl.$^6$ ............................................. G01N 21/35
[52] U.S. Cl. .................... 250/339.05; 250/339.1; 250/339.12
[58] Field of Search .................. 250/339.05, 339.1, 250/339.12, 343; 356/436

[56] References Cited

U.S. PATENT DOCUMENTS

| | | | |
|---|---|---|---|
| 4,463,261 | 7/1984 | Bowman | 250/339.1 |
| 5,155,546 | 10/1992 | Balsam et al. | 356/300 |
| 5,407,830 | 4/1995 | Altman et al. | 250/339.12 |

*Primary Examiner*—Carolyn E. Fields
*Attorney, Agent, or Firm*—Ronald D. Hantman

[57] ABSTRACT

The present invention is a method to determine the water content and/or total organic carbon content in a petrochemical stream including water, organic carbon and acid comprising irradiating a feed stream including an acid, water, and organic carbon, with optical radiation; determining the optical absorption of the feed stream for at least two selected wavelengths; and determining the weight percent of the water and/or organic carbon content from the optical absorption.

7 Claims, 5 Drawing Sheets

OPTIMIZATION OF ACID STRENGTH AND TOTAL ORGANIC CARBON IN ACID PROCESSES

This is a continuation of application Ser. No. 412,239, filed Mar. 28, 1995 now abandoned, which is a division of Ser. No. 125,060 filed Sep. 21, 1993, now U.S. Pat. No. 5,426,053 filed Jun. 20, 1995.

BACKGROUND OF THE INVENTION

The present invention is a system and method to control the acid content and/or total organic carbon of a feed stream including an acid, water and total organic carbon. The present invention permits on-line prediction of acid and TOC composition in order to adjust acid purge rates or the addition of oxidants used to remove carbon.

The process is particularly important in sulfuric acid processes. The composition of the sulfuric acid recycle stream in a sulfuric acid process is essentially comprised of sulfuric acid, water, and organic carbon (TOC). The latter component is a class of heavy hydrocarbons, a portion of which may become insoluble in the sulfuric acid and deposit in vessels, lines, or on heat exchange surfaces. Unit shutdown and maintenance are required to clean the heat exchanger surfaces in the acid concentration section.

Many petrochemical processes, such as alkylation and alcohol production, involve the partially selective extraction of certain hydrocarbon species from a hydrocarbon mixture, by reacting the mixture with aqueous acid. For example, in isopropanol production, propylene is extracted from a hydrocarbon stream with aqueous sulfuric acid. Extraction occurs due to the formation of organic sulfates. Further processing may include hydrolysis to convert the sulfates to alcohol, dehydrogenation reactions to convert the alcohol to ketone, and regeneration of the sulfuric acid for recycle to the extraction process.

Economic advantages associated with minimizing energy and feed acid consumption, and maximizing operability and product yield may be realized by monitoring and controlling the composition and properties of the streams associated with the various steps in the process. For example, a means to determine the acid strength would permit control of the addition of hydrolysis water, thereby optimizing alcohol production, while minimizing the energy expended to reconcentrate the acid for further use.

Another example is a method to determine the total organic content (TOC) of the process streams. This material includes higher molecular weight hydrocarbons formed in the sulfuric acid process, which becomes insoluble in the process stream and deposits on reactor and pipe walls. A method to quantify the amount of this material could be used to determine the optimum process condition.

The present invention is a spectroscopic method and system to determine the acid strength and total organic carbon (TOC) content of acid process streams. It is accurate, rapid, and precise and may be implemented on-line by the use of a fiber optic probe. The invention may be used to determine the acid strength by the difference between the acid and water and to indicate the TOC levels in the acid.

SUMMARY OF THE INVENTION

The present invention includes system and a method to determine the acid strength and/or total organic carbon content of a stream which includes an acid, water and organic carbon. The method includes the steps of illuminating the stream with optical radiation, determining the difference in the optical absorptivity of the stream at two selected wavelengths, and for determining the weight percent of the water and/or total organic carbon content from the difference in the optical absorptivity. We define absorptivity as the negative of the logarithm of the ratio of the transmitted light intensity to the incident light intensity, the logarithm being divided by the pathlength through the absorbing material by the light. The absorbance is the absorptivity multiplied by the pathlength.

In a preferred embodiment, the acid is sulfuric. If water content is being determined, then two selected wavelengths are about 1450 nm and 1300 nm.

If organic carbon content is being determined then the two selected wavelengths are about 546 nm and 820 nm.

For example, in isopropanol production, propylene is extracted from a hydrocarbon stream with aqueous sulfuric acid.

It is desirable to determine the total organic carbon (TOC) of the process streams. This material includes higher molecular weight hydrocarbons formed in the sulfuric acid processes, which becomes insoluble in the process stream and deposits on reactor and pipe walls. A means to quantify the amount of this material could be used to determine:

(1) the optimum rate of purging the acid from the process to achieve a target TOC level in the acid inventory, and/or (2) control the addition of anti-oxidants which may be added to convert these heavy carbon species to lighter species like CO, $CO_2$, or acetic acid which can be readily removed from the acid inventory.

DESCRIPTION OF PREFERRED EMBODIMENT

In present invention is a system and method to determine the water content and/or total organic carbon content of an acid feed stream.

The difference in absorptivity at wavelengths of 1450 nm and 1300 nm can be used to predict the water content with an accuracy of 0.8 wt % over the range of 3–100 wt %, and with an accuracy of 0.13 wt % over the more narrow range of 20–60 wt %. The precision was determined to be 0.02 wt % at a water content of 34 wt %.

Figure 1:
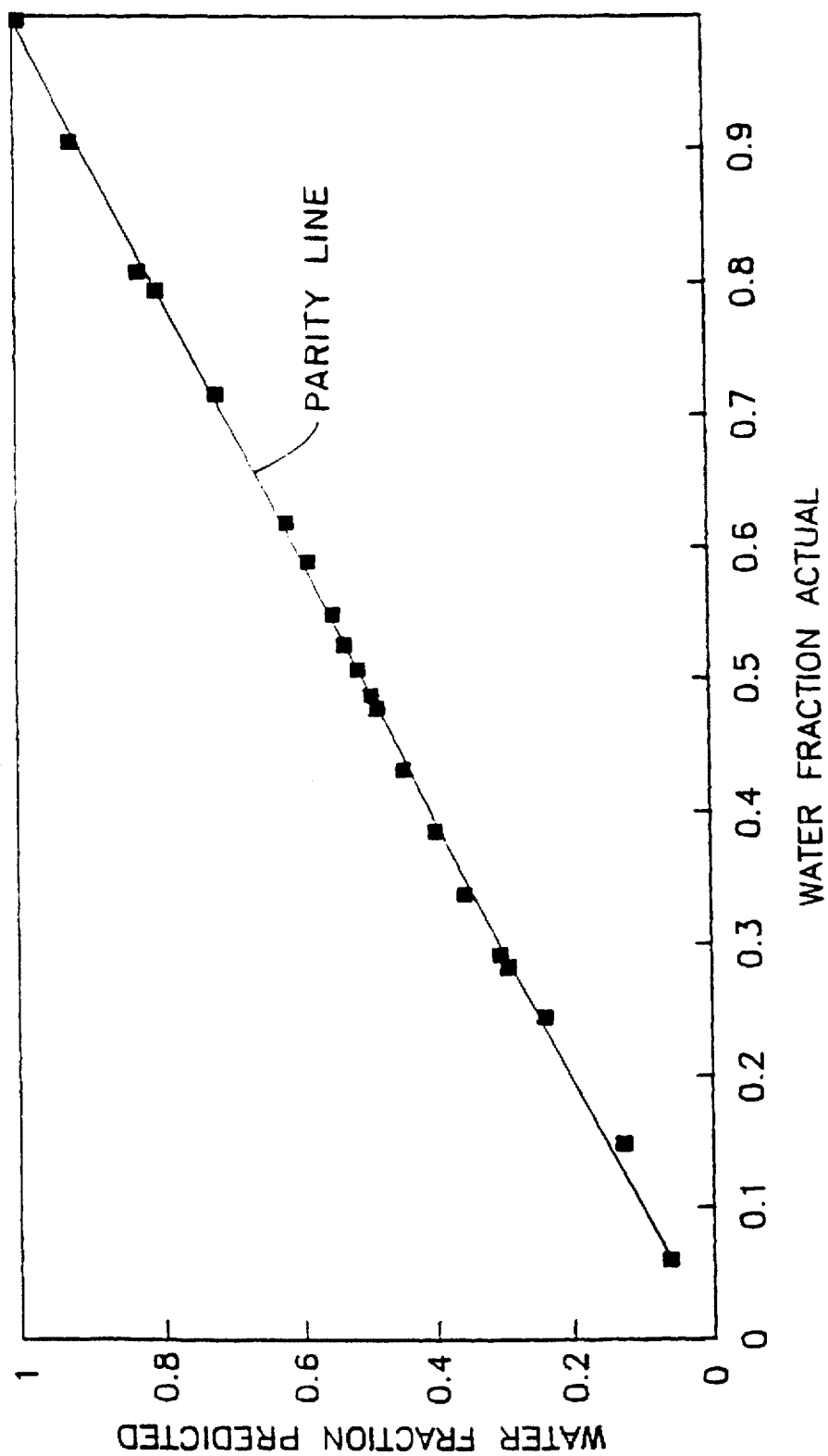
FIG. 1 shows a parity plot of the water content of several acid feed streams predicted by the present invention compared to the actual water content.

Calibration samples of known mixtures of $H_2SO_4$ and distilled water were prepared, and their spectra measured in a 2 nm pathlength cuvette over the wavelength range of 800 nm to 1600 nm in 1 nm increments. The difference in absorptivity at 1450 nm and 1300 nm was used in a regression model in which a third order polynomial was regressed against the known water content of the samples. A parity plot of the water fraction, predicted from the optical method, versus the actual water content is shown in FIG. 1.

Figure 2:
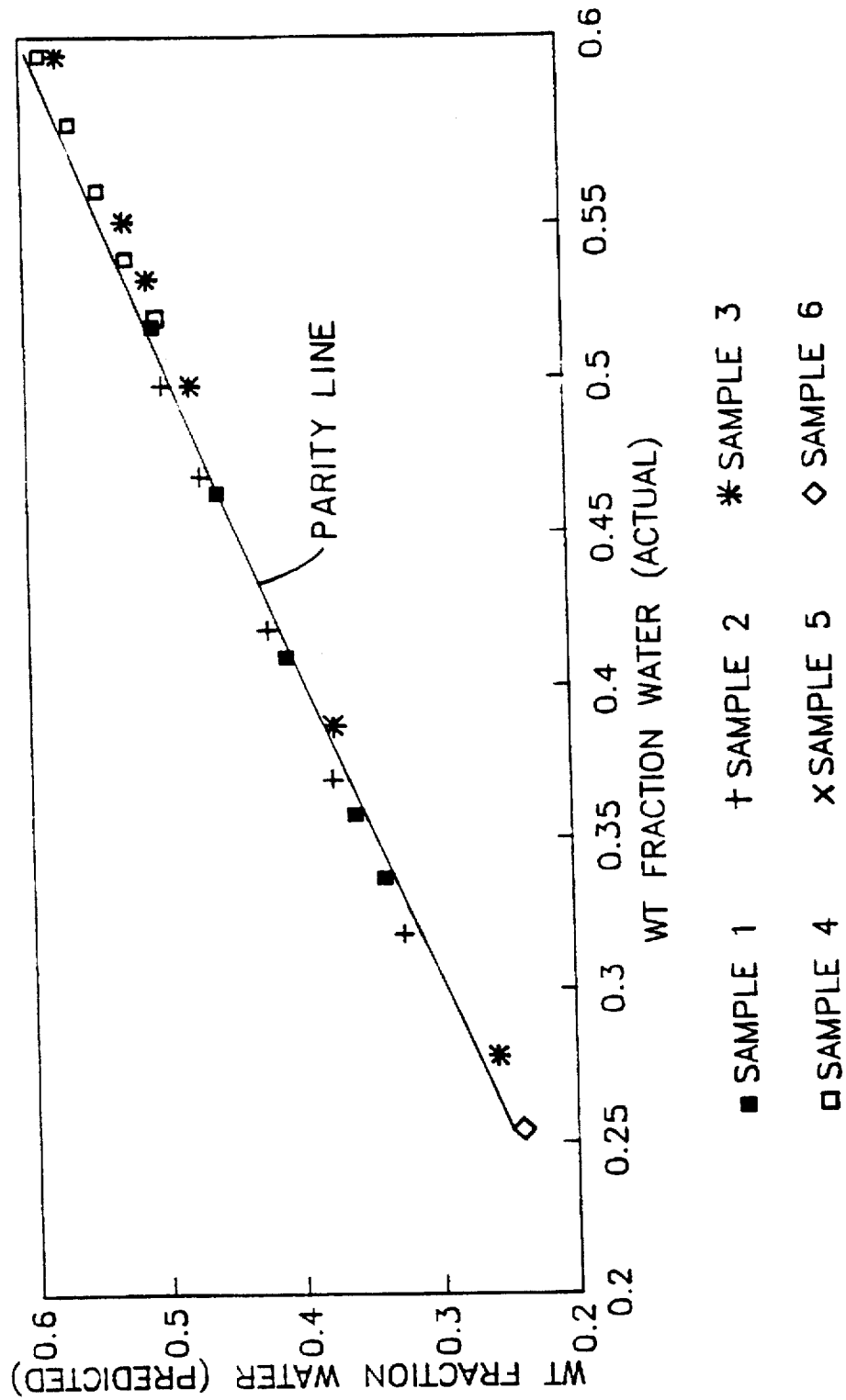
FIG. 2 shows a parity plot of the water content of several acid feed streams predicted by the present invention compared to water content determined by the Karl Fischer analysis.

The regression coefficients were used to predict the water content of six samples, whose water content was determined by Karl Fischer analysis, and 17 known water or acid dilutions of these samples. A parity plot of the spectrally-predicted versus the Karl Fischer results is shown in FIG. 2.

Figure 3:
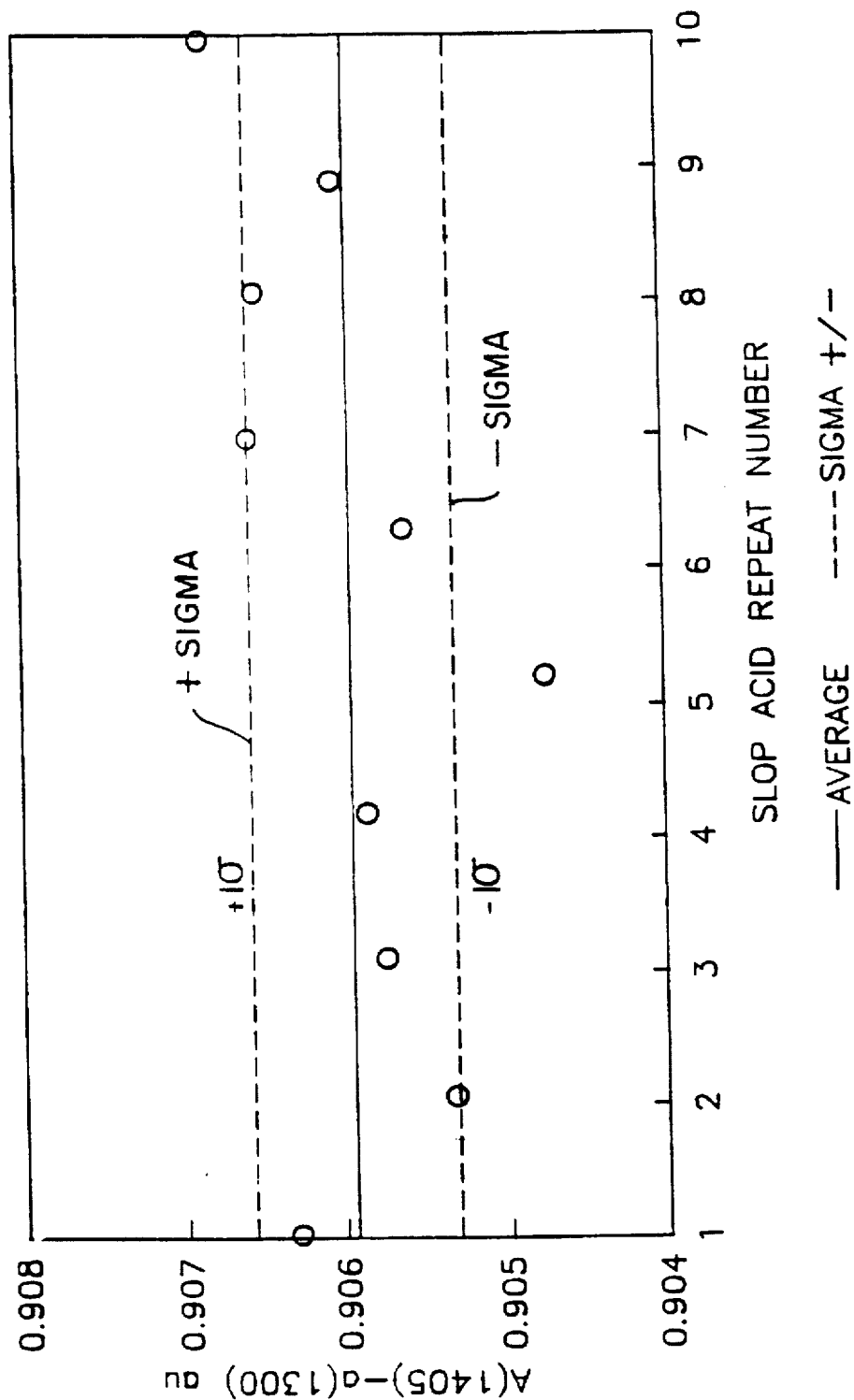
FIG. 3 shows the results of ten repeat measurements of one sample.

Ten repeat measurements were made on one sample and the average absorbance difference was found to be 0.9059 AU with a standard error of ±0.00061 AU. This absorbance difference translates into a water content of 34.9 wt % and the standard deviation of the measurements translates into a measurement precision of ±0.02%. The results of the repeat measurements are shown in FIG. 3.

Figure 4:
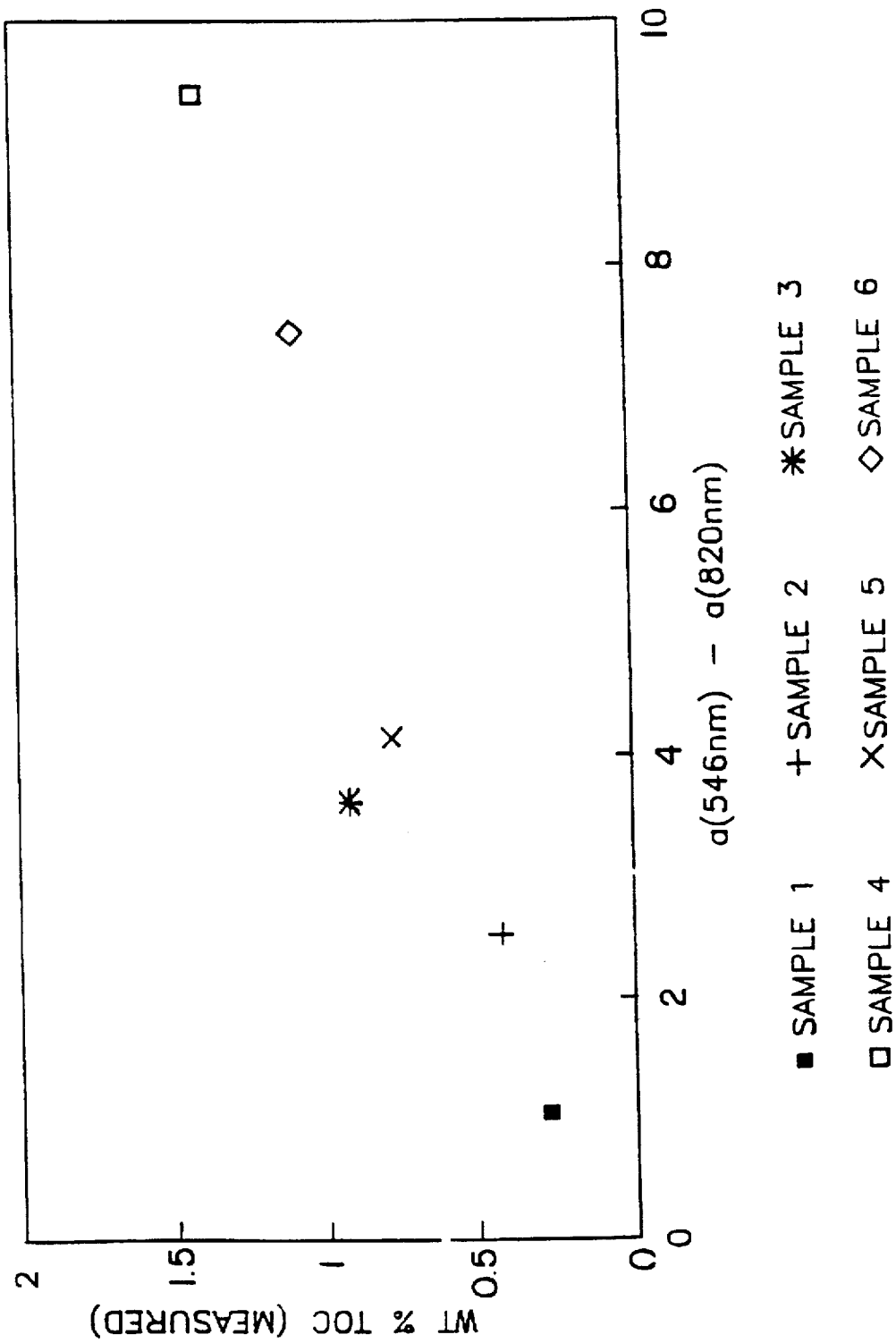
FIG. 4 shows a graph of the organic carbon content of several samples versus the absorptivity difference at wavelengths 546 nm and 820 nm.

In another aspect of this invention, the TOC can be correlated to the difference in absorptivity at wavelengths of 546 nm and 820 nm to a TOC content of 2 wt %. Spectra of six samples were measured over the spectral region of 190 nm to 820 nm with increments of 2 nm. The TOC levels of the samples were determined by a standard laboratory method. A scatter plot of the wt % TOC as measured versus the absorptivity difference is shown in FIG. 4.

For a typical stream both the water and TOC can be determined by measurements of the absorbances at the above stated wavelengths over an optical path length of 2 nm with no further dilution of the sample.

While the preferred wavelengths for the determination of water for this application are 1450 nm and 1300 nm, other wavelengths may also be used. For example, the first wavelength in the difference model for water may be chosen from 1150 nm to 1550 nm, but preferably in the ranges between 1150 nm and 1250 nm or 1350 nm and 1550 nm, and still more preferably between 1400 nm and 1500 nm. The second wavelength may be chosen to be any convenient wavelength different from the first and preferably so as to make the absorbance difference greater than 0.002 AU.

Figure 5:
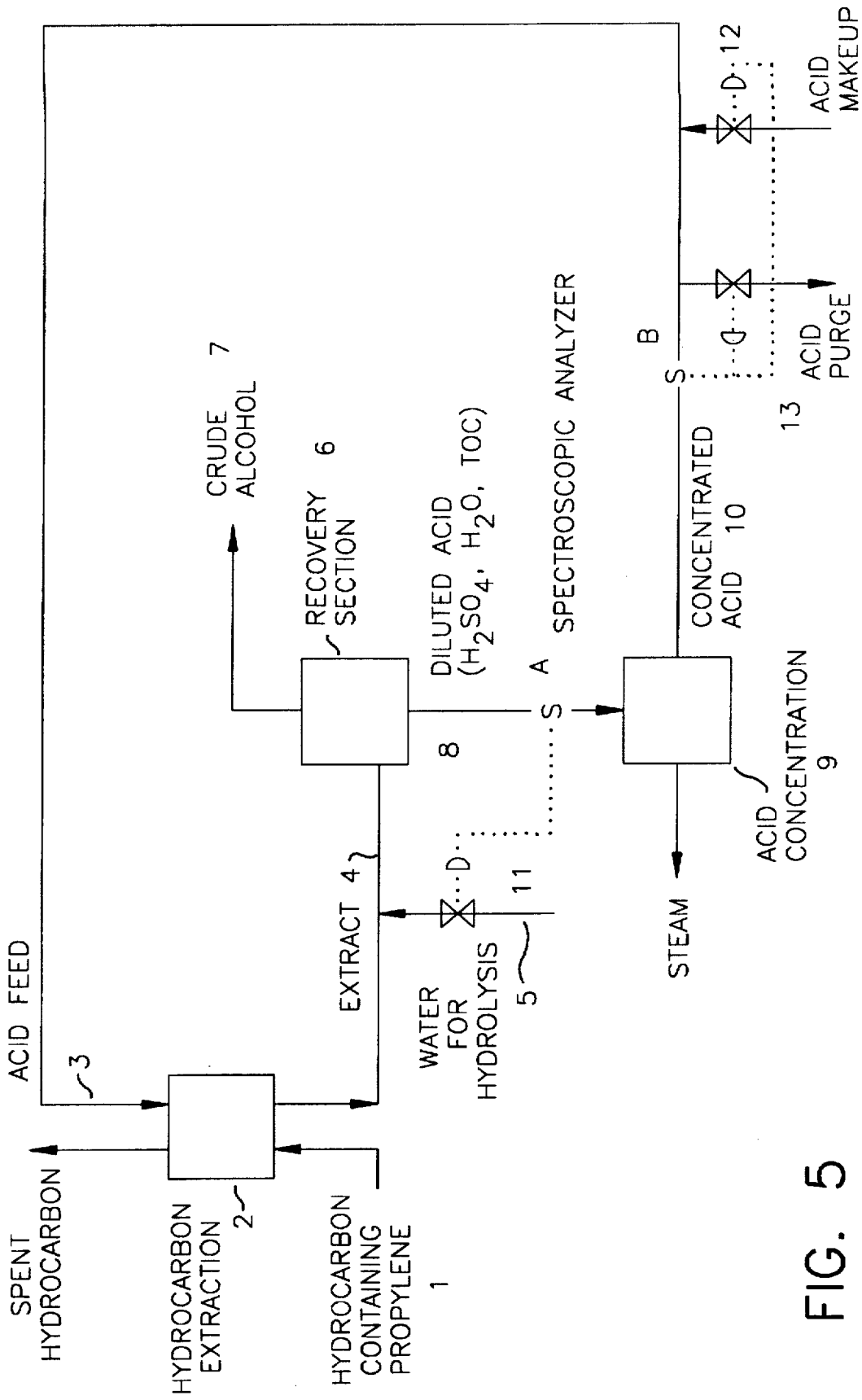
FIG. 5 shows a schematic of the optimization of a process to produce isopropanol using sulfuric acid.

The present invention also includes the optimization of processes in which it is necessary to know acid strength or total organic carbon. FIG. 5 shows a schematic of a process in which sulfuric acid is used to produce isopropanol. Propylene is extracted from a hydrocarbon feedstream (1) in one or more extraction reactors (2) by contact with an acid feed stream (3). The extract (4) is mixed with a hydrolysis water stream (5) in the alcohol recovery section (6) and is split into a crude alcohol stream (7) and a diluted acid stream (8). The diluted acid is reconcentrated in an acid concentration section (9) and the concentrated acid stream (10) is recycled as the extraction section's (2) acid feed stream (3).

Spectroscopic acid analyzing may be applied at point (A) in the dilute acid stream (8) to determine the acid strength and control the valve (11) which adjusts the addition of hydrolysis water (5) to provide an optimum acid strength in the alcohol recovery section (6).

Spectroscopic analyzing may also be applied at point (B) in the concentrated acid stream (10) to determine the acid strength and total organic carbon and control the addition of acid by controlling valve (12) or the purging of acid by controlling valve (13) in order to provide the target TOC level and acid strength, or the addition of anti-oxidants to reduce/prevent the buildup of TOC.

What is claimed is:

1. A method to determine the water content and/or organic carbon content in a stream including water, organic carbon and acid comprising:

a. irradiating a feed stream including an acid, water, and organic carbon (heavy hydrocarbons which become insoluble in a petrochemical process), with optical radiation, b. determining the optical absorption of said feed stream for at least two selected wavelengths, the selected wavelengths chosen according to whether water content or organic carbon is being determined; and c. determining the weight percent of said water and/or organic carbon content from said optical absorption.

2. The method of claim 1 wherein said two selected wavelengths are about 1300 nm and 1450 nm.

3. The method of claim 1 where said two selected wavelengths are about 546 nm and 820 nm.

4. The method of claim 1 wherein said acid is sulfuric acid.

5. A system to control acid-water content and/or organic carbon content in a petrochemical stream including water, organic carbon (heavy hydrocarbons which can become insoluble in a petrochemical process), and acid feed stream comprising:

a. means for irradiating said petrochemical stream including an acid, water, and organic carbon, with optical (visible and/or near infrared) radiation;

b. means for determining the absorptivity of said feed stream for at least two selected wavelengths, the selected wavelengths chosen according to whether water content or organic carbon is being determined;

c. means for determining the weight percent of said water and/or organic carbon content from said absorptivity wherein said water content is determined using a non-linear regression model; and d. means for determining acid strength and/or organic carbon content from said weight percents; and e. means for adjusting the water content and/or acid content of said petrochemical stream.

6. The system of claim 5 wherein said two selected wavelengths are about 1450 nm and 1300 mn.

7. The system of claim 5 where said two selected wavelengths are about 546 nm and 820 nm.

* * * * *